United States Patent [19]

Manfredi

[11] Patent Number: 4,846,816

[45] Date of Patent: Jul. 11, 1989

[54] MALE URINARY DRAIN SYSTEM

[76] Inventor: Frank A. Manfredi, 2026 W. 95th St., Cleveland, Ohio 44102

[21] Appl. No.: 710,072

[22] Filed: Mar. 11, 1985

Related U.S. Application Data

[63] Continuation-in-part of Ser. No. 447,212, Dec. 6, 1982, abandoned.

[51] Int. Cl.⁴ .............................................. A61M 5/18
[52] U.S. Cl. .................... 604/323; 604/331; 604/349; 604/353
[58] Field of Search ............... 128/DIG. 24; 604/317, 604/323, 331, 335, 347, 349, 350-353

[56] References Cited

U.S. PATENT DOCUMENTS

| | | | |
|---|---|---|---|
| 2,285,981 | 6/1942 | Johns | 604/349 |
| 2,358,440 | 9/1944 | Bowman et al. | 128/294 |
| 2,815,025 | 12/1957 | Fonton et al. | 604/327 |
| 3,421,507 | 1/1969 | Gresham | 604/349 |
| 3,835,857 | 9/1974 | Rogers et al. | 604/349 |
| 4,202,058 | 5/1980 | Anderson | 604/347 |
| 4,270,539 | 6/1981 | Frosch | 4/144.3 |
| 4,484,918 | 11/1984 | Omley | 604/349 |
| 4,540,409 | 9/1985 | Nystrom et al. | 604/349 |

FOREIGN PATENT DOCUMENTS

| | | | |
|---|---|---|---|
| 735703 | 6/1966 | Canada | 604/317 |
| 2084879 | 4/1982 | United Kingdom | 604/317 |

OTHER PUBLICATIONS

Catalog Cut "New Uro-Sans Plus Male Catheter", Mentor Corp., Minneapolis, Minn., 65411, 1982.

Primary Examiner—Jerome L. Kruter
Attorney, Agent, or Firm—Cushman, Darby & Cushman

[57] ABSTRACT

A female urinary drain assembly includes a waist band for encircling the waist of the wearer; a web of material suspended from the waist band so as to be located at the crotch of the wearer, the web having an opening through it; a urine collection funnel extending through the opening in the web and having a distal end forming a urine outlet and a proximal open end; a flange fixed on the funnel and locatable so as to bear against the inside face of the web to retain the funnel in position; and at least two leg straps connected to the web for encircling the legs of the wearer.

6 Claims, 7 Drawing Sheets

MALE URINARY DRAIN SYSTEM

This is a continuation-in-part of application Ser. No. 447,212 filed Dec. 6, 1982 now abandoned.

This invention relates to urinary collection and drain devices for male and female individuals who are partially or totally urinary incontinent.

BACKGROUND

A variety of male urinary collection and drain devices have been disclosed in the prior art. The basic purpose of such devices is to temporarily collect urine in a receptacle carried by the wearer and to provide for periodic draining of the urine from the receptacle through a manually operated valve into a toilet. When the wearer is more or less physically active, i.e. ambulatory or confined partially or wholly to a wheel chair, it is important that the device be comfortable, accommodate itself to the movements of the wearer and be easily drained, all without introducing blockage or backup of urine, leakage of urine while in place, and spillage during draining.

The devices which are commercially available and/or disclosed in the prior art serve the basic desired purpose but they tend to suffer from one or more disadvantages in the areas just mentioned. Examples of prior art devices or components thereof are disclosed in U.S. Pat. Nos. 3,336,926, 3,586,041, 3,608,552, 3,631,857, 3,661,156, 3,721,243, 3,724,461, 3,739,783, 3,749,096, 3,788,324, 3,835,857, 3,916,902, 3,926,233, 3,998,228, 3,999,550, 4,022,213, 4,055,179, 4,073,295, 4,202,335, 4,232,677, 4,343,316, 4,344,432, 4,352,356 and 4,345,342.

SUMMARY OF THE INVENTION

In accordance with one feature of the present invention a male urinary collection and drain system includes a penis sheath of special novel construction, a flexible, accordion-like outlet tube connecting the distal end of the sheath to a urine collecting bag via a positive-acting check valve which prevents reverse flow, and a flexible, accordion-like drain tube connected to the lower end of the bag and fitted with a manually operable valve. The bag is located at thigh level and is supported in that position primarily by a waist-belt, with additional stability being provided by one or more leg straps. The sheath is of special construction in that it includes one or more elastic O-rings formed integrally with its side wall, preferably at the bottoms of peripheral grooves, for forming a seal with the penis and for holding the sheath in place. In another embodiment the sheath is held in place by an assembly of waist band, pouch and leg straps, with the O-rings serving primarily a sealing function rather than a holding function. In this embodiment the sheath extends loosely through a hole in the pouch and includes a peripheral flange which lies between the pouch and the body of the wearer so as to position the sheath properly.

In accordance with another feature of the invention, a female urinary collection and drain system is provided.

DETAILED DESCRIPTION

Figure 1:
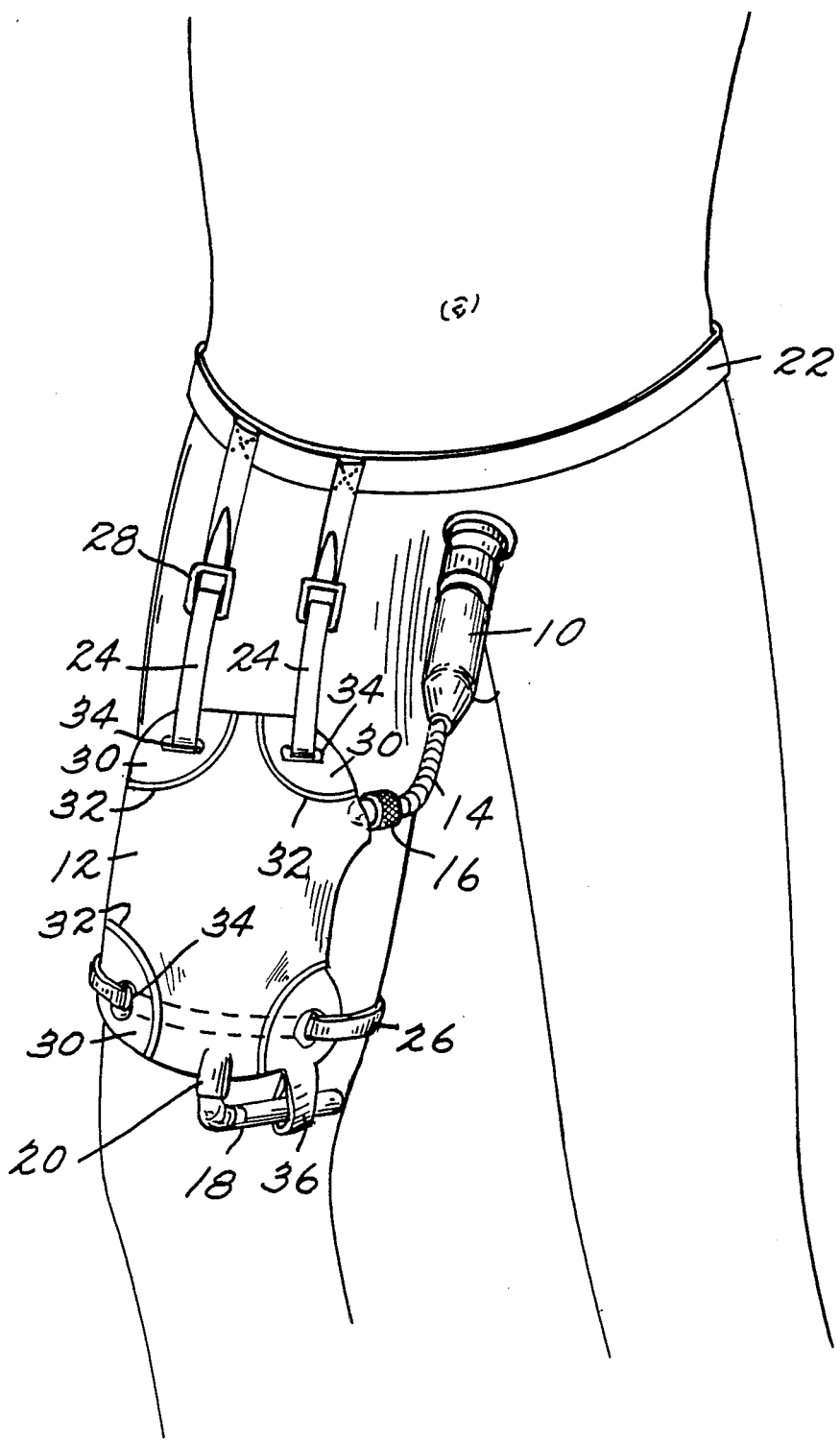
FIG. 1 is a view of a urinary collection and draining system embodying the principles of the present invention.

FIG. 1 illustrates a urinary collection and drain system which embodies several features of the invention. The major parts of the system are a penis sheath 10 or condom, a collection receptacle or bag 12, a flexible bag-inlet conduit 14 connecting the distal end of the sheath with the bag 12 via a check valve 16 which prevents back flow of urine, and a short flexible drain tube 18 connected to the lower end of the bag 12 and fitted with a manually operable drain valve 20.

As is conventional the vertical dimension of the bag 12 is somewhat greater than its horizontal dimension so that the bag 12 will lie against the front surface of one of the wearer's upper legs and at the same time have an appropriate volume. The bag 12 is thus generally rectangular, although its corners may be considerably rounded to give a generally elliptical shape. In any case the urine inlet conduit 14 connects with the bag at a location essentially at a corner (or equivalent) of the bag 12 so that the length of the conduit 14 can be as short as possible and contain as few bends as possible. This is important because it lessens the chance that the conduit 14 will become kinked during body movements and thereby block the flow of urine into the bag 12. Backup of urine into the sheath and into contact with the penis should of course be avoided in order to prevent leakage of urine and the possibility of infection.

The bag 12 must remain in essentially a fixed position because if it shifts, the conduit 14 may become kinked, collapsed or pulled loose. In the past it has been conventional to support the weight of the bag 12 by two vertically spaced-apart straps which encircle the upper leg of the wearer. This arrangement has now been found to be often unsatisfactory because either it permitted the bag to shift vertically or laterally or, if the straps were tightened enough to prevent shifting, the straps were binding and uncomfortable on the leg. Accordingly, in the system of the present invention the weight of the bag 12 is supported essentially wholly by an adjustable waist band 22 which encircles the waist of the wearer. Preferably the waist band 22 is quite narrow, for example, ½ inch to 1 inch. The bag 12 is suspended from the waist band 22 by one or more adjustable suspension straps 24 so as to be located on the front surface of the wearer's upper leg. Near the lower end of the bag 12 is an adjustable stabilizing strap 26 which encircles the wearer's leg. The straps 22, 24 and 26 are preferably of woven fabric which is elastic in the longitudinal dimension of the respective strap, and suitable buckles 28 or other adjusting means are included.

Conveniently the bag 12 is formed of soft flexible plastics material such as polyvinyl chloride, by heat-sealing the edges of two superimposed sheets of the plastic material. In the illustrated embodiment each corner area 30 of the bag 12 is strengthened and sealed from the interior of the bag 12 by an arcuate heat-sealed band 32. The area 30 can then be provided with one or more slots 34 through which the elastic straps are threaded, thereby avoiding the use of hard or bulky connections between the bag and the straps.

At the lower end of the bag 12 is a depending retaining loop 36 for loosely holding the flexible drain tube 18 in a convenient storage position, such as parallel to the lower edge of the bag 12. As illustrated in FIG. 1 the loop 36 is a permanently closed loop formed by a heat sealing operation. Alternatively the loop 36 can be formed as a strap folded over on itself with the end of the strap being releasably connected to the remainder of the strap, as with short strips of Velcro fastening fabric attached to the strap.

Figure 2:
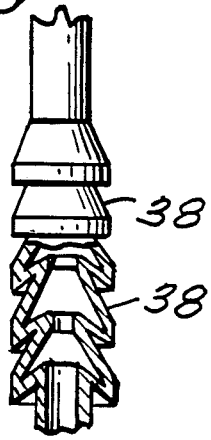
FIGS. 2, 3 and 4 are fragmentary views of tubing useful in making the connections shown in FIG. 1.
Figure 4:
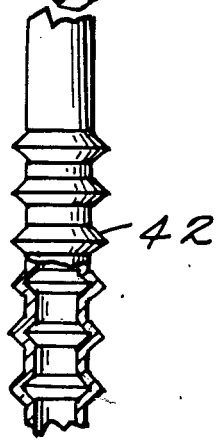
Figure 3:
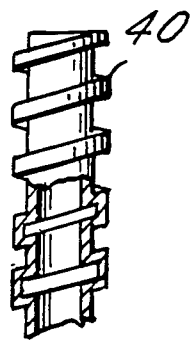

The conduit 14 and the drain tube 18 are made of naturally flexible material such as polyvinyl chloride. To enhance flexibility, prevent kinking and render the members 14 and 18 more accommodating to movements of the wearer's body these members are radially fluted, bellows-like for at least a portion of their length. The flutes may be formed so as to provide flexibility without providing any substantial axial elastic extensibility or they may be formed to provide such extensibility or they may be formed to provide both flexibility and extensibility. FIG. 2 illustrates a tube construction which is particularly suitable for providing resilient axial extensibility, the tube wall having flaps 38 extending outwardly and at an acute angle to the axis of the tube. FIGS. 3 and 4 illustrate tube constructions which are suitable for providing flexibility. FIG. 3 shows closely-spaced sharp-edged pleats 40 set at an angle to the tube axis, and FIG. 4 shows radially extending pleats 42 with rounded edges.

Figure 5:
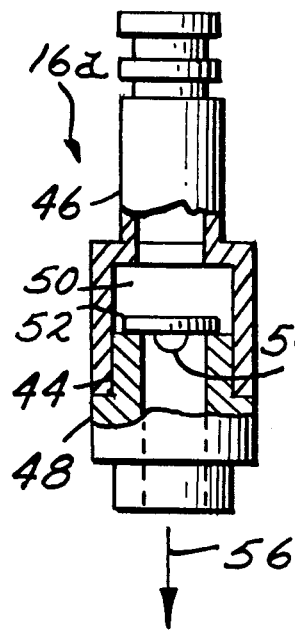
FIGS. 5 and 6 are partial sectional views of two embodiments of check valves.
Figure 6:
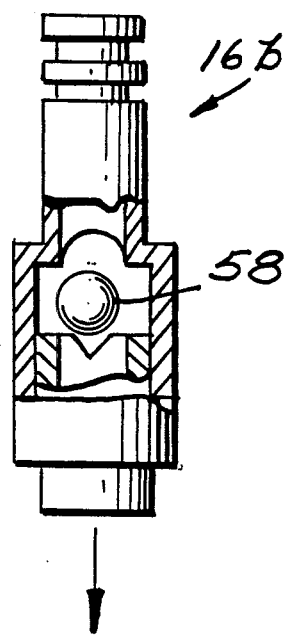

FIGS. 5 and 6 illustrate check valves 16a and 16b which are particularly suitable for use in the invention. The valve 16a includes a tubular piece 44 telescoped into a tubular piece 46 to the extent permitted by an external shoulder 48 on the piece 44. An internal cavity 50 is formed by and between the pieces 44 and 46 and residing in the cavity 50 is a floating closure disc 52. The diameter of the disc 52 is greater than the diameter of the bore in the piece 46 and smaller than the outer diameter of the end of the piece 44. The end of the piece 44 has a transverse groove 54 which permits flow in the direction of the arrow 56, i.e. into the bag 12. Reverse flow out of the bag 12 will force the disc 52 into sealing engagement with the bore in the piece 46 and thereby prevent flow into the conduit 14. The FIG. 6 construction is similar to FIG. 5 except that the closure member is a ball 58.

Figure 7:
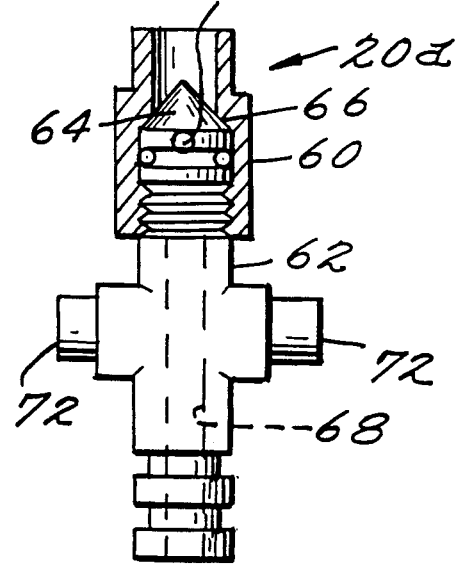
FIG. 7 is a partial sectional view of a drain valve.

FIG. 7 illustrates a particularly suitable drain valve 20a for use in the invention. As illustrated the valve is a two-piece assembly having an interiorly-threaded tubular part 60 and an externally-threaded tubular part 62 threaded into the piece 60. The inner end 64 of the part 62 is conical and is engageable with a complementary annular valve seat 66 on the part 60. The bore 68 of the piece 62 terminates in one or more transverse openings 70 located below the cone 64. The valve is shown in a closed position; slight unscrewing of the part 62 will disengage the cone 64 from the valve seat 66 and permit flow through the valve. It is preferred to connect the piece 60 to the bag 12 and the piece 62 to the drain tube 18, but this relationship can be reversed. The part 62 has a laterally projecting finger piece 72 which can be grasped by the fingers to aid in unscrewing the part 60. Only a slight twist, for example, one-half turn, is necessary to open the valve.

Figure 8:
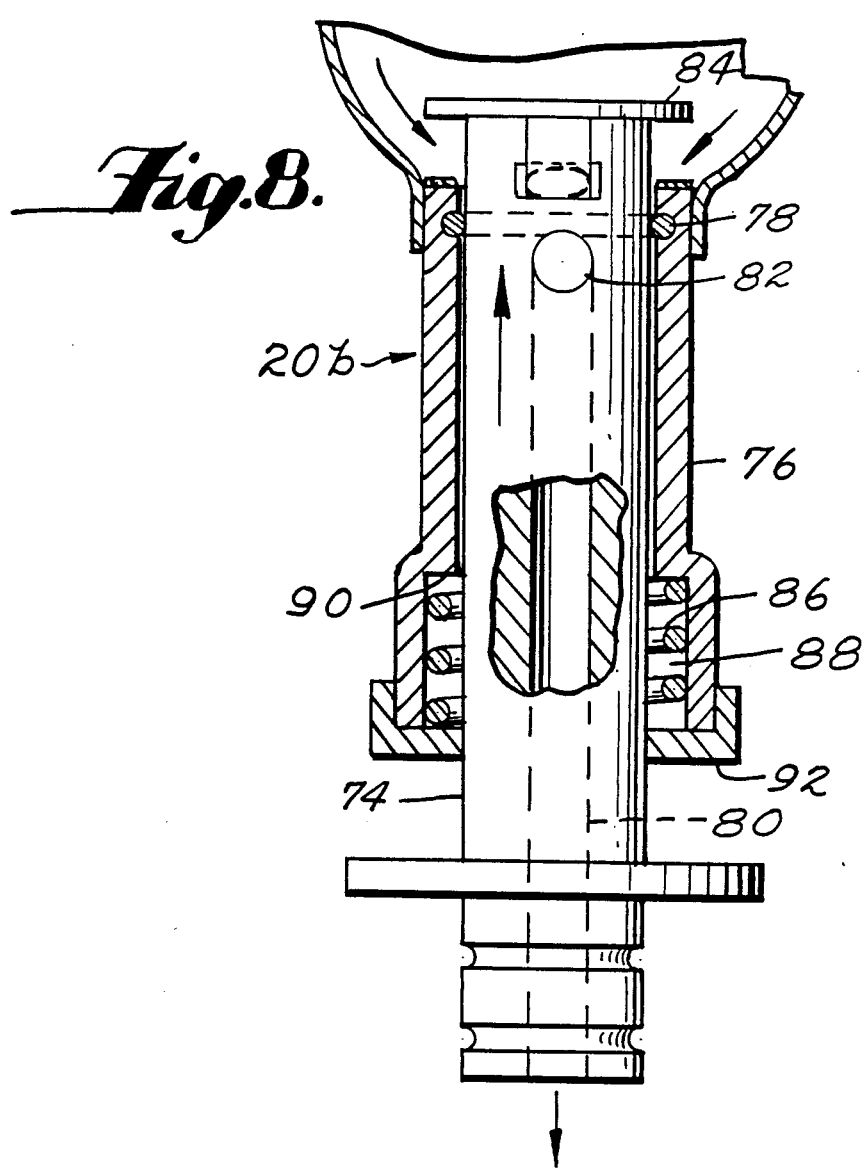
FIG. 8 is a partial sectional view of another drain valve.

FIG. 8 illustrates another drain valve 20b. This valve comprises a tubular plunger axially slidable within a barrel 76, with an O-ring 78 forming a seal between the exterior of the plunger 74 and the interior of the barrel 76. The upper end of the barrel 76 is in communication with the bag 12. The bore 80 in the plunger 74 terminates in one or more transverse openings 82 located below the O-ring 78. The upper end of the plunger 74 carries a closure disc 84 the lower surface of which is engageable with the adjacent end of the barrel 76. A compression spring 86 is located in a cavity 88 formed by and between the plunger 74 and the barrel 76. The spring 86 surrounds the plunger 74 and bears against an internal shoulder 90 on the barrel 76 and a cap 92 on the barrel 76. The spring 86 normally biases the plunger 74 downwardly so that the closure disc 84 seals with the upper end of the barrel 76, preventing flow. When the plunger 74 is manually moved upwardly against the spring bias, the disc 84 moves away from the end of the barrel 76 and after further movement the aperture 82 passes above the O-ring 78, with the result that liquid will pass into the aperture 82 and downwardly through the bore 80. The O-ring 78 can be carried in a peripheral groove in the plunger 74, and in such a construction flow through the valve will occur when the O-ring 78 rises above the end of the barrel. The plunger 74 is illustrated in FIG. 8 in an intermediate position.

Figure 9:
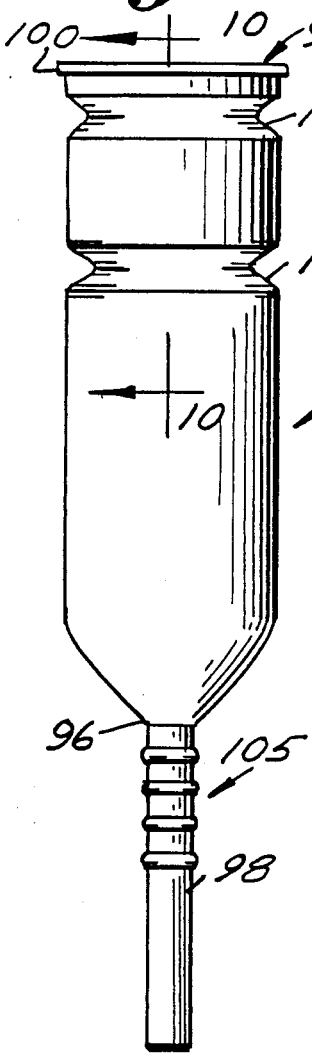
FIG. 9 is a view on an enlarged scale, of the sheath of FIG. 1.

FIG. 9 illustrates, on an enlarged scale, the penis sheath 10 of FIG. 1. The sheath is a tubular member molded of flexible elastic material such as rubber having an open proximal end 94 and a distal end 96 integral with a flexible conduit 98. The proximal end 94 has a conventional bead 100 to reinforce the sheath. Axially spaced from the end 94 are two circumferential grooves 102 molded into the material of the sheath 10. The bottom wall of each groove forms an integral O-ring 104 which forms a seal with the penis and also holds the sheath 10 in place. To this end the bottom wall is of greater thickness than the side walls of the groove and the adjacent wall of the sheath. With this construction the bottom wall, when radially expanded, produces a greater inward contracting force than do the axially adjacent portions of the sheath wall. The connector tube 98 includes a bellows section 105 immediately adjacent the distal end of the sheath 10.

Figure 11:
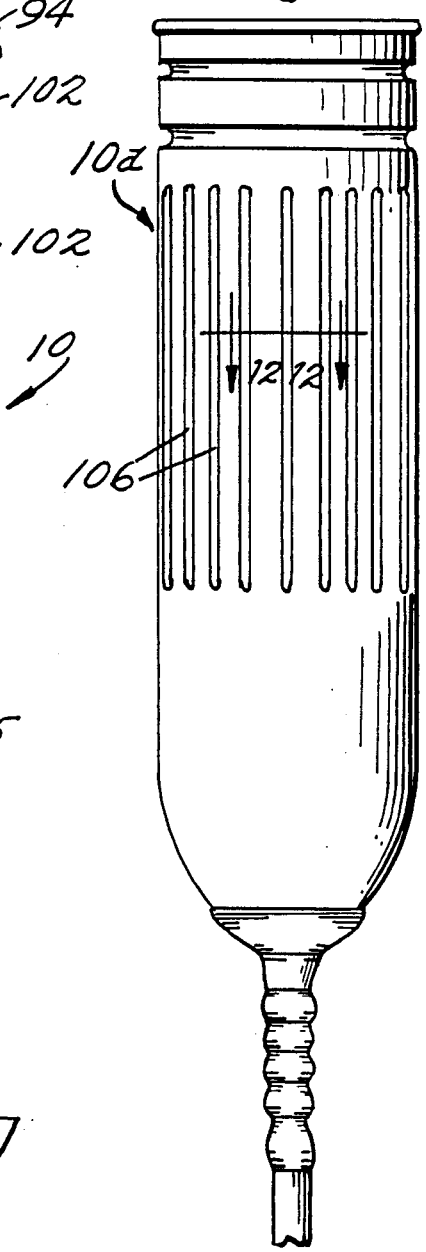
FIG. 11 is a view of a longitudinally pleated sheath.
Figure 13:
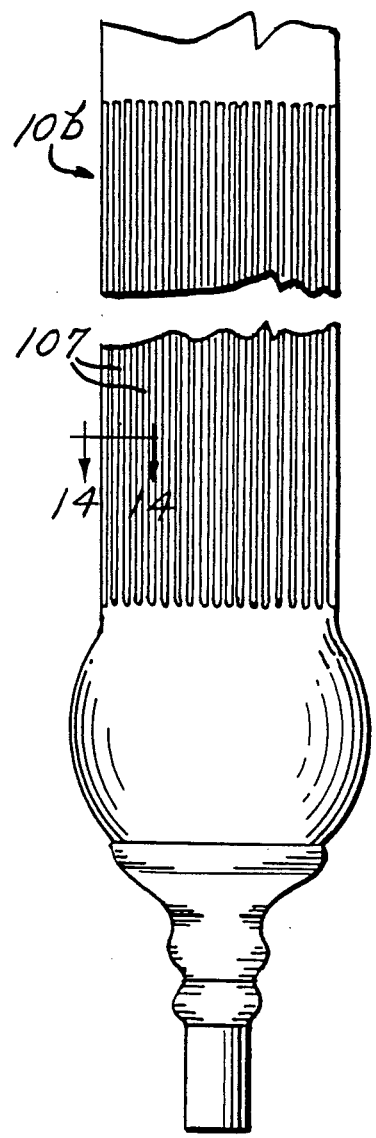
FIG. 13 is a view of another longitudinally pleated sheath.
Figure 10:
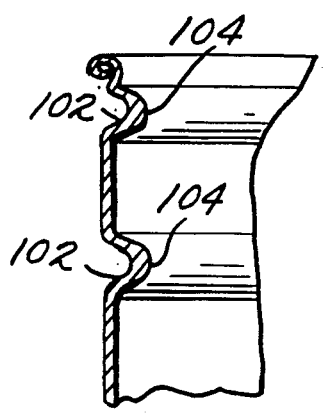
FIG. 10 is a sectional view taken on the line 10—10 of FIG. 9.
Figure 12:
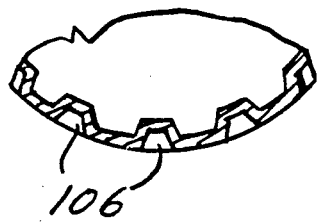
FIG. 12 is a sectional view taken on the line 12—12 of FIG. 11.
Figure 14:
FIG. 14 is a sectional view taken on the line 14—14 of FIG. 13.

FIGS. 11 and 12 illustrate a penis sheath 10a which is similar to the sheath 10 of FIG. 9 except that the sheath 10a is longitudinally pleated at 106 to allow greater radial extension. The pleats 106 are provided on the entire circumference. FIGS. 13 and 14 illustrate a similar sheath 10b having continuous fine pleats 107 entirely around the circumference of the sheath.

Figure 15:
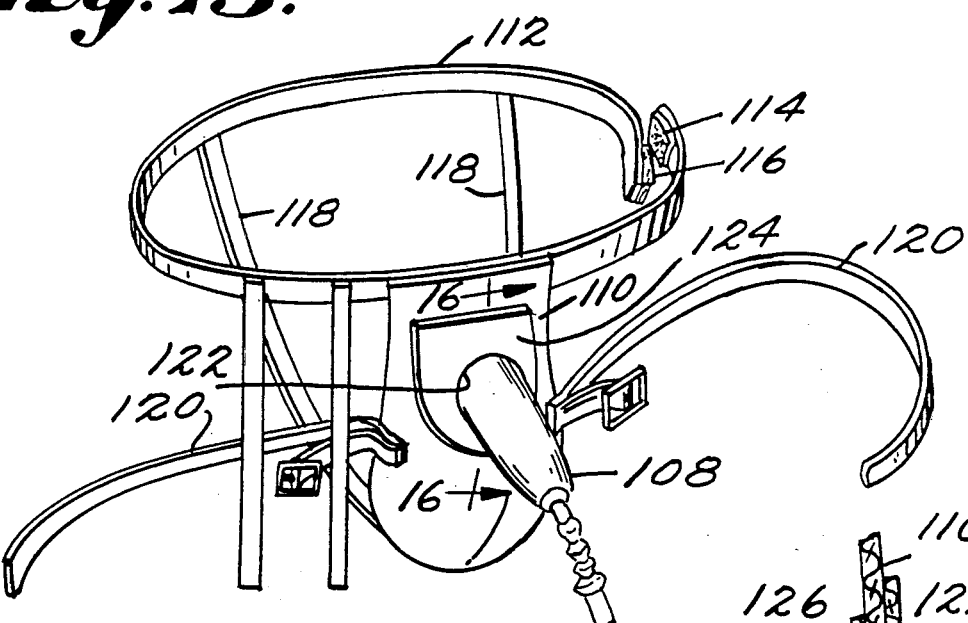
FIG. 15 is a perspective view of another draining system.
Figure 16:
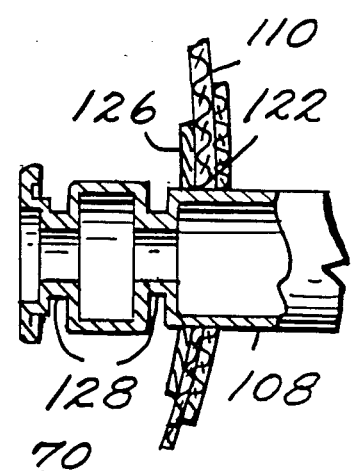
FIG. 16 is a sectional view taken on the line 16—16 of FIG. 15.

FIG. 15 illustrates a draining system having a penis sheath 108 releasably carried by a fabric pouch 110 which is waist-supported. The upper end of the pouch is directly attached to a thin (e.g. ½ inch to 1 inch wide) elastic belt 112 having Velcro fasteners 114, 116 at its ends. The lower end of the pouch 110 is connected in a conventional manner to the rear part of the waist strap by elastic straps 118. Each side of the pouch 10 is provided with an adjustable strap 120 adapted to encircle one of the wearer's legs. The purpose of the straps 120 is to hold the pouch 110 snugly to the wearer's body in order to hold the removable sheath 108 in place, as described subsequently.

The front of the pouch 110 is provided with an aperture 122 around which a piece of reinforcing fabric 124 may be attached if necessary. The sheath 108 extends through the aperture 122. A radial flange 126 is fixed to the sheath near its proximal end and lies against the inner surface of the pouch 110 but is not attached thereto. The flange 126 is substantially stiffer than the material of the sheath 108 and resiliently restrains or prevents the sheath 108 from being pulled out of the pouch 110. The sheath 108 can, however, be easily removed in a rearward direction from the pouch 110 when the assembly is not being worn. When the assembly is being worn, with the leg straps 120 secured about the legs of the wearer, the flange 126 is pressed between the pouch 110 and the wearer's body and thereby stabilizes the position of the sheath 108. The sheath preferably includes molded-in O-rings 128 of the kind previously described In this embodiment the O-rings 128 serve essentially only as urine seals, as the sheath is held in position by the straps.

Figure 17:
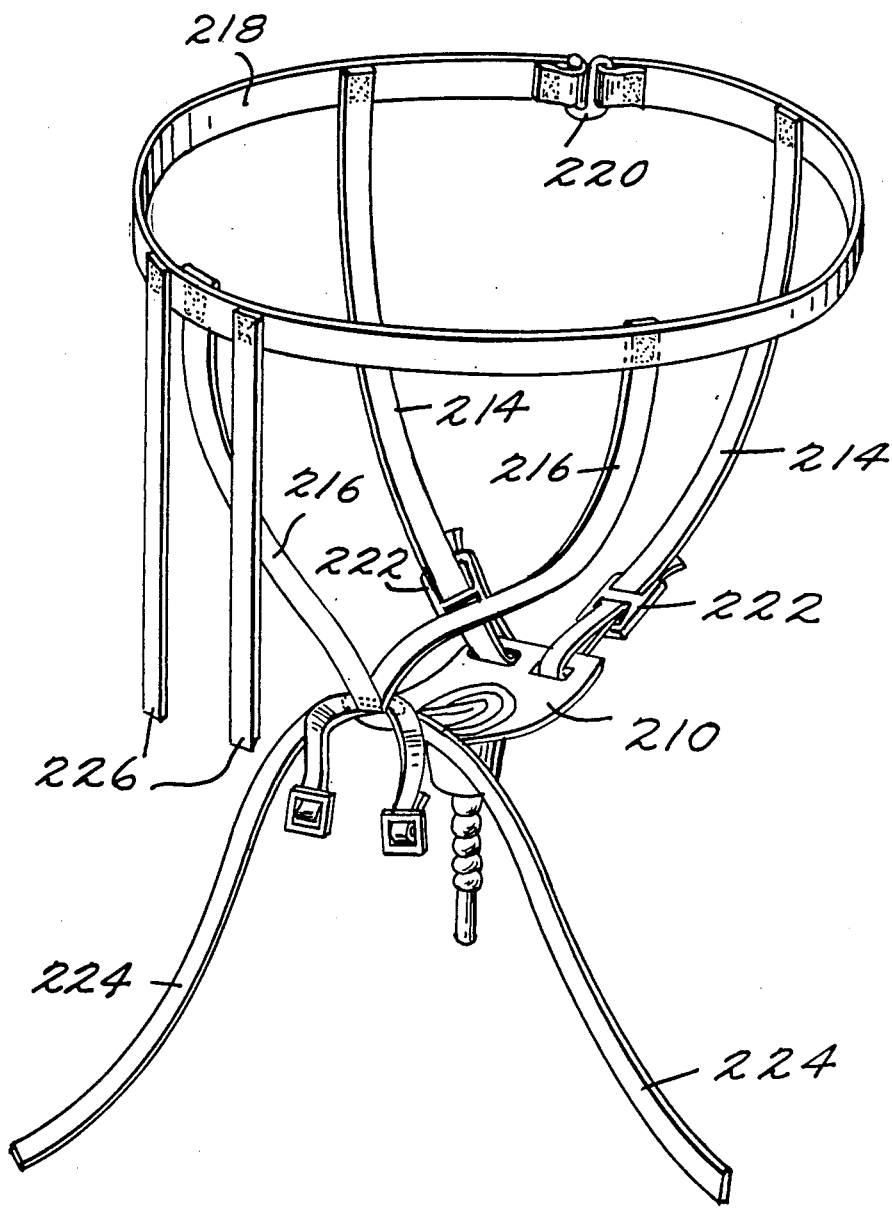
FIG. 17 is a perspective view of parts of a female urinary drain system corresponding to the view of FIG. 15 and, like FIG. 15, not showing the collecting bag and drain tube.
Figure 18:
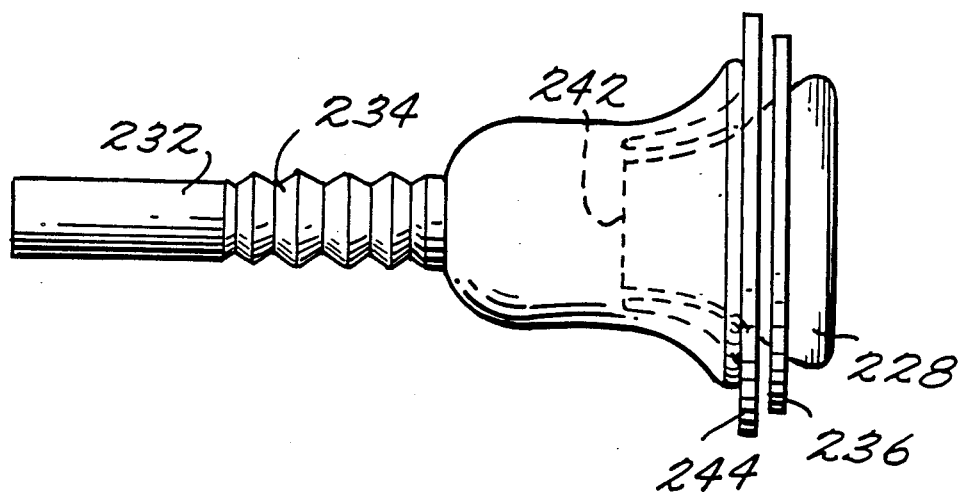
FIG. 18 is a side view of the urine collecting device of the female drain system of FIG. 17.
Figure 19:
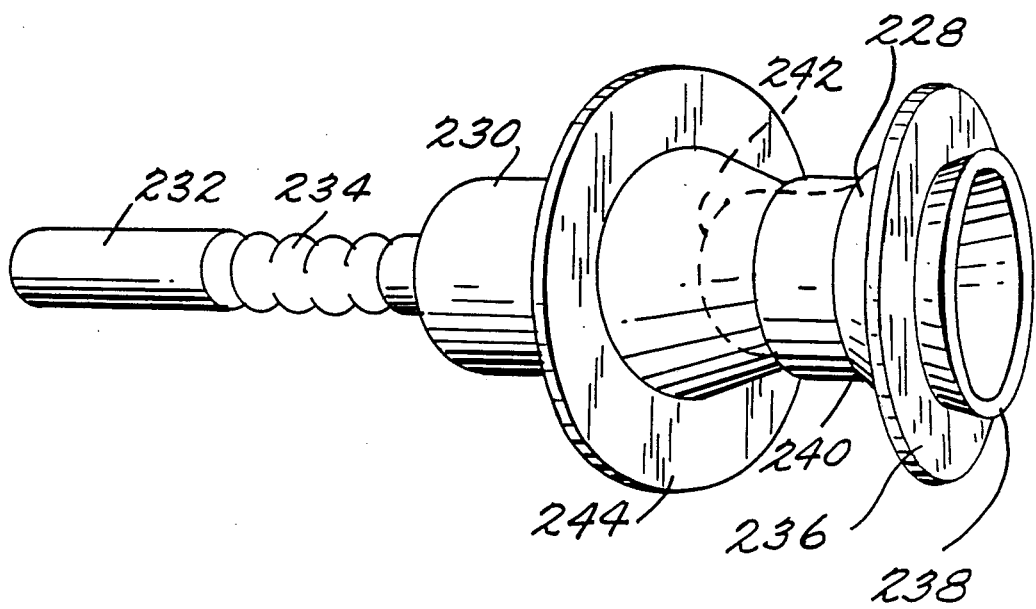
FIG. 19 is a perspective view of the device of FIG. 18, shown in its expanded form.

FIGS. 17 to 19 show an adaptation of the drain system of FIGS. 1 and 15 for use by a woman. Corresponding to the pouch 110 of the system shown in FIG. 15, that of FIG. 17 has an approximately square web 210 of soft textile fabric through a central hole of which is inserted the urine collection device 212 illustrated in FIGS. 18 and 19. The web 210 is attached by four straps 214, 216 to a resiliently extensible waist belt 218 which is here shown with a simple hook and loop connector 220 for its ends but which may alternatively be of adjustable length. The rear straps 2 are shown with optional length-adjustment buckles 222. Instead the front straps 216 may have length-adjustment means, or all four straps 214,216 may be adjustable in length.

As in the system of FIG. 15, also attached to the web 210 are two strap and buckle arrangements 224 for attaching around the upper legs of the wearer. By suitable attachment and adjustment of the belt and the straps, the web 210 can be made to lie comfortably against the crotch of the wearer.

Shown hanging from the belt 220 are two vertical straps 226 for attachment to the collecting bag, e.g. via buckles in the manner of the straps 24 shown in FIG. 1. The bag is suspended from the belt 220 by these straps 226, in use. In this embodiment the collecting bag, its drain tube and valve and its manner of support on the user's leg are exactly as shown in FIG. 1.

The collection device of FIGS. 18 and 19 is in the form of a flanged funnel 228 of relatively thick, soft rubber, e.g. sponge rubber of a latex like material, attached to a flanged sleeve portion 230 formed of thin resilient flexible rubber sheet and integral with a narrower conduit portion 232 leading to the collecting bag via a check valve, like the conduit 14 of FIG. 1. Also, like the conduit 14 of FIG. 1, the conduit 232 is partly of bellows-like construction 234, to allow easy flexing and length variation without kinking or strain.

The funnel 228 is of sufficient rigidity to hold its shape approximately when in use without imposing discomfort on the user and has an exterior flange 236 slightly spaced from its oval open end 238, so that the funnel can be arranged by the user comfortably with the end 238 appropriately placed in relation to the urethra to collect the urine. The funnel 238 is attached to the end of the sleeve 230 at seal 240 closely behind the flange 236 but extends a substantially distance further into the sleeve 230 to its distal end 242 which is freely located within the sleeve, so that when the sleeve and funnel are in their telescoped arrangement as shown in FIG. 18, the end 242 is spaced from the walls of the sleeve thereby inhibiting collection of liquid in this region and also flow of liquid back up the funnel 228. This reduces the risk of infection.

The sleeve 230 has a relatively rigid rubber flange 244 welded to its exterior (so that the interior of the sleeve 230 has no discontinuities which might collect urine). In use this flange 244 lies against the inner face of the web 210, and the flange 236 of the funnel lies against it. The funnel is thus held in place by the web 210.

Figure 20:
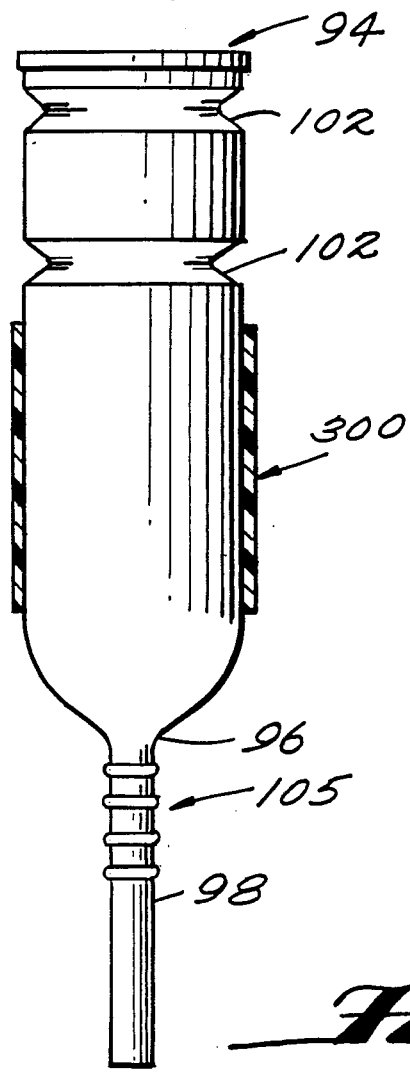
FIG. 20 is longitudinal sectional view of a sheath fitted with an outer tube which serves as an aid in applying the sheath to the penis.
Figure 21:
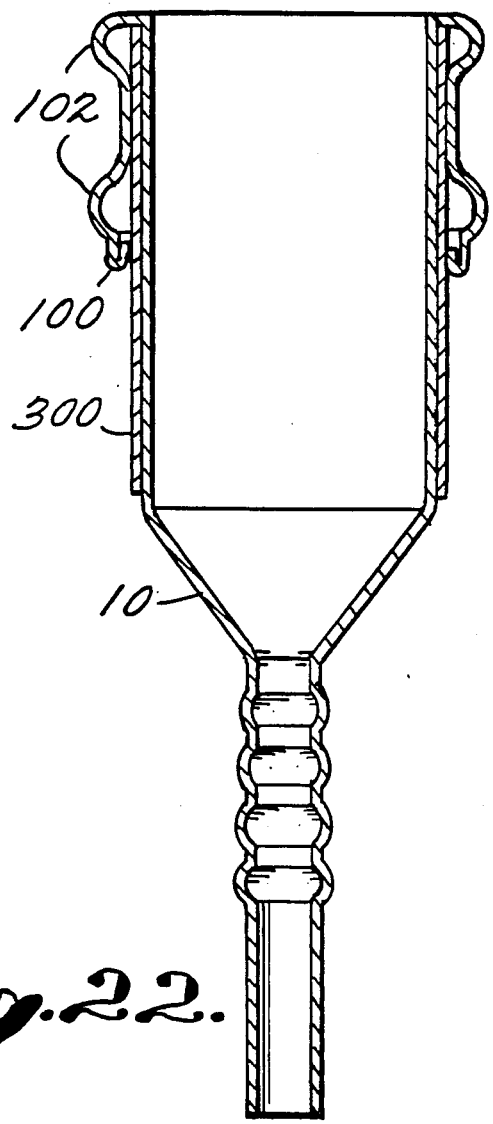
FIG. 21 is a view of the FIG. 20 assembly with the sheath folded over the outer tube.

FIGS. 20 and 21 illustrate the penis sheath 10 of FIG. 9 fitted with an aid for applying the sheath to a penis. The aid includes a clamping member in the form of a tube 300 made of a material more rigid than the flexible sheath 10 and removably fitted over the sheath 10. Before applying the sheath 10 to a penis the upper portion of the sheath 10 is folded down over the tube 300 as shown in FIG. 21. The tube 300 is then grasped manually and slid over the penis thereby carrying the sheath over the penis. The sheath 10 is then held in place manually and the tube 300 is slid off of the sheath 10. The tube 300 may be conveniently made of semi-rigid or rigid plastic or of cardboard. The wall of the tube 300 may be continuous around the sheath 10 or it may have a longitudinal slot extending from one end to the other.

Figure 22:
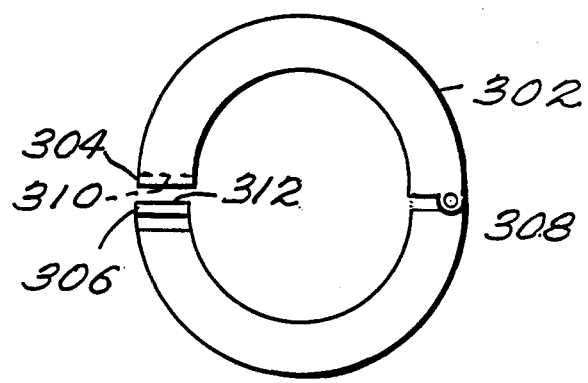
FIG. 22 is a plan view of a different form of aid.

FIG. 22 illustrates an aid in the form of a two-piece clamping ring 302 having free ends 304 and 306 and a hinge 308 connecting the other ends of the two pieces. The free ends 304,306 are provided with some means for releasably holding the ring 302 in a closed position, such as a slot 310 in one end 304 and a complementary rib 312 in the other end 306. In use, the sheath 10 is placed within the ring 302 and the free ends 304,306 of the ring 302 are manually moved together to cause the rib 312 to enter the slot 310 and be frictionally held therein. The assembly is then slid over the penis after which the ring 302 is manually opened and removed, leaving the sheath on the penis.

What is claimed is:

1. A condom or penis sheath for use in a urinary draining assembly comprising a tubular member of molded flexible elastic material, said member having a side wall of single thickness throughout its length and said member having an open proximal end and a distal end having connected thereto a flexible urine discharge conduit of lesser diameter than the tubular member, said side wall having, near but spaced axially from its proximal end, at least one circumferential groove having a bottom wall located radially inwardly relative to the remainder of said side wall; a solid elastic circumferential ring of lesser inside diameter than the remainder of said side wall molded integrally with the material of said side wall at the bottom of said groove, said ring having a bottom wall of a radial thickness greater than thickness of the remainder of said side wall and being radially outwardly stretchable and having a radially inwardly contracting force greater than the remainder of said side wall so as to function in use as an O-ring which, by contraction of the ring, holds the sheath to the penis and forms a seal therewith; a removable aid for facilitating application of the sheath to a penis, said aid including a removable encircling clamp member of greater rigidity than the sheath surrounding at least a substantial portion of the circumference of the sheath thereby providing a gripping surface enabling manual manipulation of the sheath;

said encircling member being a ring-shaped clamp having free ends movable towards and away from each other.

2. A condom or penis sheath for use in a urinary draining assembly comprising a tubular member of flexible elastic material, said member having an open proximal end and a distal end which merges into a flexible urine discharge conduit of lesser diameter than the tubular member, at least a portion of the length of said conduit being circumferential pleated, accordion-like, to enhance lateral flexibility of the conduit relative to said tubular member, the wall of said tubular member being a single thickness wall of said flexible elastic material and having a diameter such that said wall must be stretched radially outward to permit the sheath to be drawn over the penis, said wall forming, at a location near but spaced axially from said proximal end, at least one groove having opposed side walls the thickness of which is essentially the same as the thickness of the wall of said tubular member and a bottom wall located radially inward of the remainder of the wall of said tubular member, said bottom wall having a greater thickness than said side walls of the groove and forming a solid elastic circumferential ring of lesser inside diameter than the remainder of said tubular member, said ring being radially outwardly stretchable and having a radially inward contracting force greater than that of the remainder of the wall of said tubular member so as to function in use as an O-ring which, by its contraction, holds the sheath to the penis and forms a seal therewith.

3. A sheath as in claim 2 including a second circumferential groove and associated circumferential ring of lesser diameter than said tubular member, said second groove and associated ring being axially spaced from the first-named groove and associated ring.

4. A male urinary collecting and drainage assembly comprising: a sheath as in claim 2; a urine collecting bag of vertically elongated, generally rectangular shape constructed of flexible material; at least one leg strap carried by the bag at a location near the lower end of the bag for encircling a leg of the wearer; a waist strap for encircling the waist of the wearer; suspending means connected between the waist strap and the upper end of the bag for supporting essentially the entire weight of the bag from the waist strap; a bag inlet conduit connected to said discharge conduit and to said bag at a location near the upper corner which in use of the bag is closest to the inside of the wearer's leg; a urine drain conduit communicating with the lower end of the bag, said drain conduit having a longitudinal portion which is circumferentially pleated, accordion-like, to enhance flexibility; and a manually operable flow valve cooperating with said drain conduit for draining urine from the bag.

5. A condom of penis sheath for use in a urinary draining assembly comprising a tubular member of flexible elastic material, said member having an open proximal end and a distal end which merges into a flexible urine discharge conduit of lesser diameter than the tubular member, the wall of said tubular member being a single thickness wall of said flexible elastic material and having a diameter such that said wall must be stretched radially outward to permit the sheath to be drawn over the penis, said wall forming, at a location near but spaced axially from said proximal end, at least one groove having opposed side walls the thickness of which is essentially the same as the thickness of the wall of said tubular member and a bottom wall located radially inward of the remainder of the wall of said tubular member, said bottom wall having a greater thickness than said side walls of the groove and forming a solid elastic circumferential ring of lesser inside diameter than the remainder of said tubular member, said ring being radially outwardly stretchable and having a radially inward contracting force greater than that of the remainder of the wall of said tubular member so as to function in use as an O-ring which, by its contraction, holds the sheath to the penis and forms a seal therewith.

6. A male urinary collecting and drainage assembly comprising: a sheath as in claim 5; a urine collecting bag of vertically elongated, generally rectangular shape constructed of flexible material; at least one leg strap carried by the bag at a location near the lower end of the bag for encircling a leg of the wearer; a waist strap for encircling the waist of the wearer; suspending means connected between the waist strap and the upper end of the bag for supporting essentially the entire weight of the bag from the waist strap; a bag inlet conduit connected to said discharge conduit and to said bag at a location near the upper corner which in use of the bag is closest to the inside of the wearer's leg, at least a portion of the length of said inlet conduit being circumferentially pleated, accordion-like, to enhance flexiblity; a urine drain conduit communicating with the lower end of the bag, said drain conduit having a longitudinal portion which is circumferentially pleated, accordion-like, to enhance flexibility; and a manually operable flow valve cooperating with said drain conduit for draining urine from the bag.

* * * * *